United States Patent [19]

Pittman

[11] Plant 4,062

[45] June 21, 1977

[54] KALANCHOE PLANT

[76] Inventor: Roy Nyal Pittman, 4211 Washington, Amarillo, Tex. 79110

[21] Appl. No.: 588,004

[22] Filed: June 18, 1975

[51] Int. Cl.[2] ..... A01H 5/02

[52] U.S. Cl. ..... Plt./68

[58] Field of Search ..... Plt./68

*Primary Examiner*—Robert E. Bagwill

*Assistant Examiner*—James R. Feyrer

*Attorney, Agent, or Firm*—Ely Silverman

EXEMPLARY CLAIM

1. A new and distinct variety of Kalanchoe plant substantially as herein disclosed characterized by the unique combination of flowers borne clearly above the foliage, said flowers being of large and uniform size, graceful, cusped petal shape and distinctive, attractive and uniform bright contrasting crimson flower coloring contrasting with a large green glossy regular leaf and upright sturdy branches.

2 Drawing Figures

The present invention relates to a new and distinct variety of Kalanchoe plant discovered by me in my greenhouse in Amarillo, Tex. where it grew to a height of about 10 inches as a seedling.

These Figures show a typical specimen plant of my new Kalanchoe variety as depicted in bloom and in color as nearly true as is reasonably possible in illustrations of this character.

I found and observed and grew this seedling in my greenhouses in Amarillo, Tex. when it flowered at a height of about 10 inches.

Figure 1:
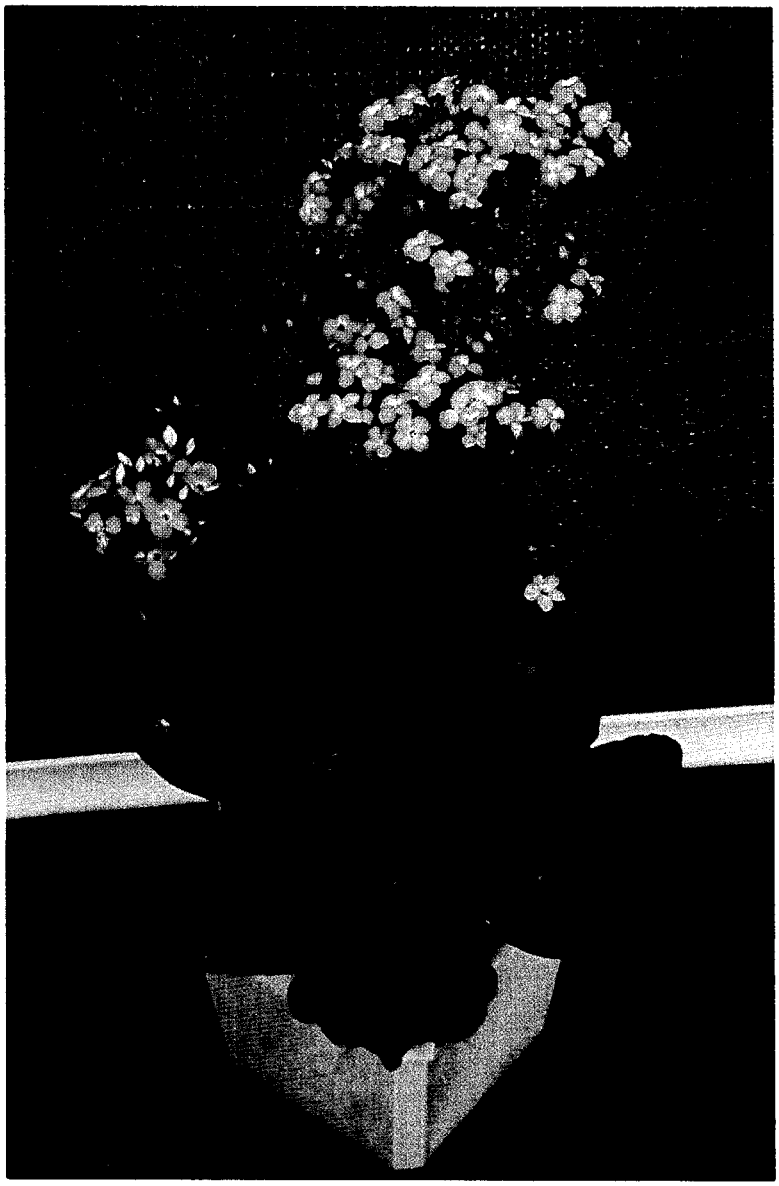
FIG. 1 is an overall side oblique view of the full plant typically grown.
Figure 2:
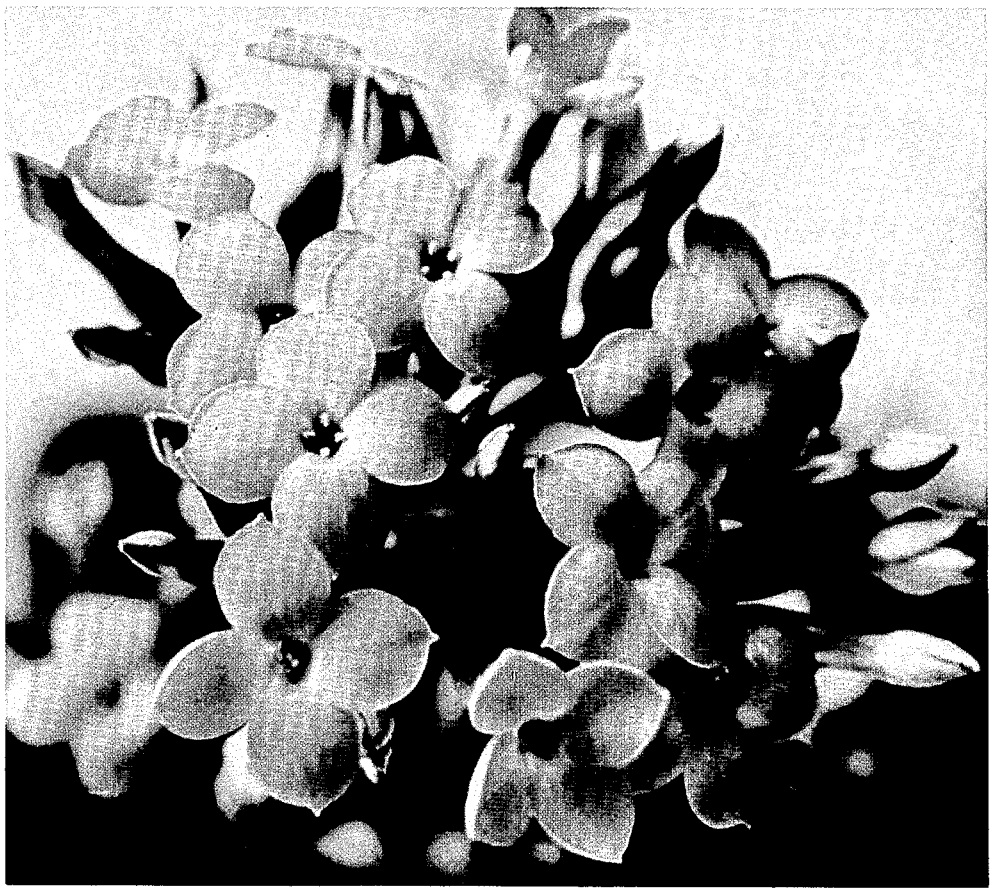
FIG. 2 is a close-up view of a flower cluster to illustrate the individual flower shape.

As a result of observation of its distinguishing characteristics, I started asexual reproduction of my new Kalanchoe by cuttings at my greenhouse in Amarillo, on Mar. 21, 1974. The range of day temperature was 70° F. to 85° F.; the range of night temperature was 60° F. to 70° F. The length of daylight hours was from 7:30 A.M. to 5:30 P.M. The length of night hours was from 5:30 P.M. to 7:30 A.M.

The present invention is a selection from a self of a cross between a tall red scented pollen parent of Kalanchoe variety of unknown origin and, as a seed parent, a Kalanchoe variety known as "Gold Dust," described in U.S. Plant Pat. No. 3,765 issued Aug. 19, 1975, entitled "Kalanchoe Plant."

As a result of such breeding, I found an improved Kalanchoe plant variety which is distinguished from its parents, as well as from other varieties, as evidenced by the following unique and commercially valuable combination of principal characteristics which are outstanding in the new variety:

1. The flower is very highly colored and unusual in coloring and fully formed compared with known varieties of Kalanchoe plants and has a distinctive and attractive crimson flower coloring.

2. A profusion of long lasting blooms which are borne on short sturdy flower stems clearly above the foliage.

3. A self-branching, upright and compact habit of growth, 8 to 12 inches high from the top of the uppermost flower on the plant to the level of the top of the ground supporting the plant when mature.

4. An attractive, flexible foliage of medium size and fern green color.

5. An early blooming habit, about 1 week earlier than the pollen parent.

6. An ability to respond to photoperiod manipulation for year around flowering.

7. It is especially suited as a potted plant.

8. The foregoing characteristics and distinctions come true and are transmitted through succeeding vegetatively propagated generations by direct rooting of cuttings.

The following is a detailed description of my new Kalanchoe plant variety with color terminology in accordance with the Royal Horticultural Society Colour Chart, (RHS) except where general terms of ordinary dictionary significance are obvious.

Locale where grown and observed: Amarillo, Potter County, Tex.

Parentage: A selection from a self of a cross between a Kalanchoe variety known as "Gold Dust" (U.S. Plant Pat. No. 3,765 issued Aug. 19, 1975) with an unpatented Kalanchoe variety, the former being the seed parent and the latter being the pollen parent. The pollen parent is an unnamed tall, red, scented Kalanchoe variety of unknown origin.

Foliage:

*Size.*—Length 3 inches when mature; width 2½ inches when mature.

*Color.*—Top: Fern green. Bottom: Fern green. The young leaves may have a wine red net effect on their bottom.

*Shape.*—Oblong with obtuse tip and truncate base.

*Quantity.*—Abundant.

*Texture.*—Top, glossy and smooth. No veins visible. Bottom, smooth.

*Margin.*—Regular crenate in youngest; undulate almost entire in oldest.

Stem: Pale green.

Disease resistance: Superior resistance to common Kalanchoe diseases than old standard varieties, as determined by comparison with other such Kalanchoe varieties grown under the same greenhouse conditions in Randall County, Tex.

Flowers: Complete, larger than usual for Kalanchoe.

*Size.*—Diameter: about ½ inch (12–13mm). Depth: about ½ inch (12–13mm). Petals: Length: 3/16 inch (5–6mm). Width: 3/16 inch.

*Form.*—Compound umbel; section petals united in four cusped sections; ovary superior.

*Color.*—Upper side crimson, RHS 40A. Under side mandarin red, RHS 29C-D. Throat: buttercup yellow, RHS 1C.

*Stamen.*—Few (4) and symmetrical.

*Blooming period.*—4 to 6 weeks.

Plant:

*Growth habit.*—Upright, self-branching, compact, short (from 8 to 12 inches tall when mature), medium vigor.

*Form.*—Upright, compact, much-branched.

*Rooting habit.*—Roots easily from any part of stem forming a fibrous root system.

*Blooming season.*—Adaptable to year around flowering by day length manipulation.

*Blooming habit.*—Flowers naturally about December 1st.

Fruit: None.

Hardiness: Good in range from 55° F. to 100° F. during day.

General observations: This plant has all the qualities for a good potted plant with short, upright compact growth with distinctively colored and attractive flowers.

I claim:

1. A new and distinct variety of Kalanchoe plant substantially as herein disclosed characterized by the unique combination of flowers borne clearly above the foliage, said flowers being of large and uniform size, graceful, cusped petal shape and distinctive, attractive and uniform bright contrasting crimson flower coloring contrasting with a large green glossy regular leaf and upright sturdy branches.

* * * * *